United States Patent [19]

Levy

[11] 4,409,691
[45] Oct. 18, 1983

[54] FOCUSSABLE INTRAOCULAR LENS

[76] Inventor: Chauncey F. Levy, 1299 Portland Ave., Rochester, N.Y. 14621

[21] Appl. No.: 317,240

[22] Filed: Nov. 2, 1981

[51] Int. Cl.³ .......................... A61F 1/16; A61F 1/24
[52] U.S. Cl. .......................................................... 3/13
[58] Field of Search .............................................. 3/13

[56] References Cited
U.S. PATENT DOCUMENTS

| 4,074,368 | 2/1978 | Levy, Jr. et al. | 3/13 |
| 4,253,199 | 3/1981 | Banko | 3/13 |
| 4,285,072 | 8/1981 | Morcher et al. | 3/13 |

Primary Examiner—Ronald L. Frinks
Attorney, Agent, or Firm—Hoffman Stone

[57] ABSTRACT

An intraocular lens that provides accommodation in response to contraction and relaxation of the ciliary body. Accommodation is achieved by motion of the lens, or of an element of a lens system, alternately toward and away from the fovea. Means are provided for biasing the lens, or the movable element, toward the fovea so that when the ciliary body is fully relaxed the lens is at its closest position to the fovea, and as the ciliary body contracts it counters the bias and causes the lens to move away from the fovea and toward the cornea.

5 Claims, 5 Drawing Figures

FOCUSSABLE INTRAOCULAR LENS

BRIEF DESCRIPTION

This invention relates to a novel intraocular lens that is capable of providing accommodation responsively to contraction and relaxation of the ciliary body.

In the normal eye the crystalline lens is self-biased toward a spherical shape, that is, toward maximum refraction, and for distance viewing it is radially tensioned, and thereby flattened, by relaxation of the ciliary body.

The lens of the present invention operates on a basically different principle, one generally similar to the usual focussing arrangement in photographic cameras. It achieves accommodation by adjustment of its focal distance, the spacing between the lens and the fovea. The lens in spring biased toward its distance focus position, where it remains so long as the ciliary body remains relaxed. When the ciliary body contracts it compresses the spring bias, moving the lens away from the fovea to provide accommodation for near viewing.

The bias may be supplied by radially extending struts molded integrally with the lens, which struts extend slightly rearwardly from the lens to engage, or, rather, to be engaged by the ciliary body. When the ciliary body contracts it thus drives the outer ends of the struts radially inwardly causing their inner ends to move forwardly, carrying the lens forwardly and thereby increasing its focal distance.

Alternative forms of the invention may include miniature lens systems of two or more lens elements in accordance with the designer's choice. In the usual case only one of the elements of a system is arranged for movement responsively to the ciliary body, while the other, or others, of the individual elements remain in fixed position.

The lens of the invention is preferably placed in the natural capsule that previously held the crystalline lens, and the zonules are left in place, unless they are somehow damaged, in which case they may be replaced by an air filled flexible toroid. The capsule serves to hold the lens, and especially the struts, in proper position for engagement by the ciliary body. As in the usual modern practice only a portion of the front wall of the capsule is removed, and a small window is cut in its rear wall. The struts extend to the perimeter of the capsule, and the entire structure is retained by the capsule.

DETAILED DESCRIPTION

Representative embodiments of the invention will be described in detail in conjunction with the accompanying drawing, wherein.

Figure 1:
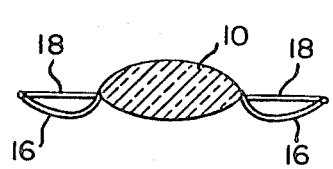
FIG. 1 is a cross sectional view of an intraocular lens in accordance with a first embodiment of the invention.
Figure 2:
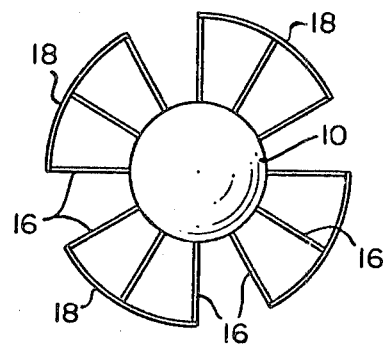
FIG. 2 is a front elevational view of the lens shown in FIG. 1.
Figure 3:
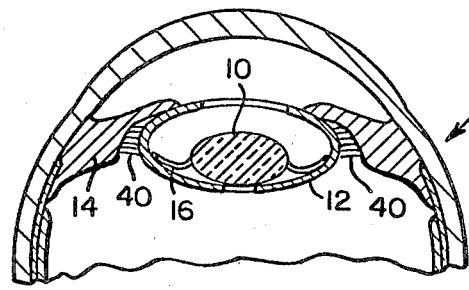
FIG. 3 is a fragmentary sectional view of an eye in which the lens shown in FIGS. 1 and 2 has been implanted.

Referring now to FIGS. 1, 2, and 3, the lens according to the first embodiment of the invention comprises a central refractive element 10 about six to eight millimeters in diameter and having a refractive power selected by the surgeon to provide normal distance vision when it is implanted in the capsule 12 and the ciliary body 14 is relaxed. Radially extending struts 16 are molded integrally with the refractive element 10 and are terminated at their outer ends by any desired blunt abutment means such as the arcuate rim portions 18 illustrated. The struts are just long enough so that the terminations 18 are in light pressure contact with the perimeter of the capsule 12 when the lens is implanted in the eye 20. The struts lie at an angle to the central plane of the refractive element 10 so that the terminations 18 lie slightly closer to the fovea when the lens is implanted than does the refractive element 10.

When the ciliary body 14 contracts, as it normally does when the eye tries to focus on a nearby object, it drives the outer ends of the struts 16 radially inwardly, thereby forcing the lens 10 forwardly, away from the fovea, and, as the ciliary body relaxes the struts act as springs to retract the refractive element 10 back to its original position for distance focus.

It is preferred to make the refractive element 10 as small as is practicable, that is, as small as is needed to admit enough light for practical vision. This is to minimize resistance to motion of the refractive element by the aqueous humour, or by the saline solution that may replace it. It is presently thought that about six millimeters diameter is close to the optimum size.

Figure 4:
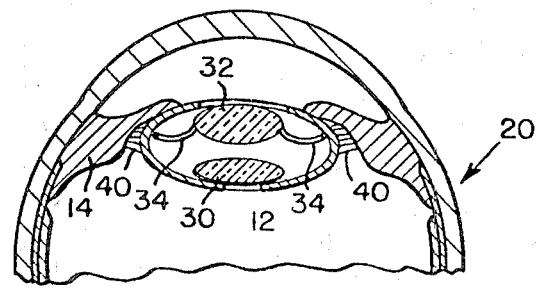
FIG. 4 is a fragmentary sectional view of an eye in which a lens according to a modified form of the invention has been implanted.

An intraocular system comprising two lens elements 30 and 32, respectively, according to the invention is illustrated in FIG. 4. It comprises a posterior lens element 30 of significantly smaller diameter than the capsule 12. It is positioned centrally within the capsule 12 in contact with the posterior wall thereof. It remains in position because of the smallness of forces available to dislodge it as compared to its natural adherence to the capsule wall.

The second element 32 lies in the anterior chamber of the eye, and is generally similar to the lens 10 shown in FIGS. 1, 2, and 3, being supported on struts 34 that extend rearwardly and radially outwardly through the fornix in the anterior wall of the capsule 12 into engagement with the perimeter of the capsule. The powers of the lenses 30 and 32, and the initial spacing between them are selected by the optical designer to provide the desired focussing action in response to motion of the movable lens 32. A large variety of choices are available.

Figure 5:
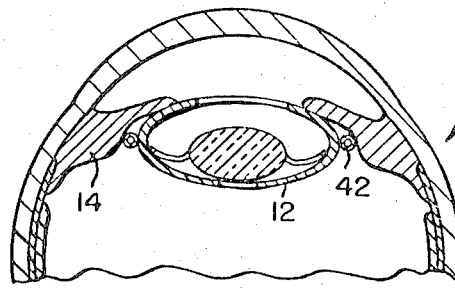
FIG. 5 is a fragmentary sectional view of an eye in which the zonules have been replaced by an air filled torus.

As shown in FIG. 5, the zonules 40 (FIGS. 3 and 4, and not shown in FIG. 5) may be removed and replaced by an air filled torus 42 that acts as a cushion between the lens 10 and the ciliary body 14, and also serves to keep the lens 10 in proper position relative to the ciliary body. The torus 42 may be made of any flexible and impervious sheet material that is compatible with body tissues and fluids.

What is claimed is:

1. An intraocular lens capable of providing accommodation comprising a lens element, and spring biasing means operative between said lens element and the ciliary body when the lens element is implanted for alternately moving the lens element bodily all parts in the same direction toward a first position relative to the fovea when the ciliary body is relaxed and bodily all parts in the same direction toward a second position farther from the fovea in response to contraction of the ciliary body.

2. An intraocular lens in accordance with claim 1 wherein said spring biasing means comprises struts extending radially outwardly from said lens element toward the ciliary body and rearwardly so that their outer ends lie closer to the fovea than does said lens element, the angle between the lengths of said struts and the central plane of said lens being resiliently yieldable in response to contraction of the ciliary body.

3. An intraocular lens according to claim 1 wherein said lens element and said spring biasing means are arranged for implantation within the capsule that holds the crystalline lens in the normal eye.

4. An intraocular lens system capable of providing accommodation comprising a first lens element for implantation in fixed position in the eye, a second lens element to be spaced from said first lens element along the main optical axis of the eye, and spring biasing means operative between said second lens element and the ciliary body when the second lens element is implanted for alternately moving said second lens element bodily all parts in the same direction toward a first position along the optical axis when the ciliary body is relaxed and bodily all parts in the same direction toward a second position when the ciliary body contracts, the optical specifications of said lens elements being selected so that the focal length of the system is longer when said second element is toward said second position than when it is toward said first position.

5. An intraocular lens system according to claim 4 wherein said first lens element is arranged for implantation within the capsule of the eye against the posterior wall thereof, said second lens element and said spring biasing means are arranged for implantation in the anterior chamber with said spring biasing means extending into the capsule and engaging the perimeter thereof, and said second position of said second element is farther from the fovea than said first position.

* * * * *